United States Patent [19]

Cartmell et al.

[11] Patent Number: 5,154,706
[45] Date of Patent: Oct. 13, 1992

[54] WOUND DRESSING FOR DEEP WOUNDS

[75] Inventors: James V. Cartmell, Xenia; Michael L. Wolf, West Milton; Michael J. Allaire, Cincinnati, all of Ohio

[73] Assignee: NDM Acquisition Corp., Minneapolis, Minn.

[21] Appl. No.: 741,349

[22] Filed: Aug. 7, 1991

[51] Int. Cl.⁵ ............... A61F 13/02; A61F 13/00; C08L 15/00; A61B 19/08
[52] U.S. Cl. .................. 604/307; 604/304; 602/43; 602/48; 523/111; 128/850; 128/851
[58] Field of Search ........ 128/155, 156, 888, 849-851; 604/304, 307, 904; 523/111; 602/41-43, 48

[56] References Cited

U.S. PATENT DOCUMENTS

| | | |
|---|---|---|
| 2,328,795 | 9/1943 | Finks .................... 604/904 |
| 2,381,621 | 8/1945 | Schmelkes et al. . |
| 3,220,960 | 11/1965 | Wichterle et al. . |
| 3,875,937 | 4/1975 | Schmitt et al. . |
| 3,949,742 | 4/1976 | Nowakowski . |
| 4,214,582 | 7/1980 | Patel . |
| 4,224,945 | 9/1980 | Cohen . |
| 4,226,232 | 10/1980 | Spence . |
| 4,393,048 | 7/1983 | Mason, Jr. et al. . |
| 4,496,535 | 1/1985 | Gould et al. ........... 523/111 |
| 4,499,896 | 2/1985 | Heinecke . |
| 4,538,603 | 9/1985 | Pawelchak et al. . |
| 4,657,006 | 4/1987 | Rawlings et al. . |
| 4,706,662 | 11/1987 | Thompson . |
| 4,765,478 | 8/1988 | Bringloe . |
| 4,977,892 | 12/1990 | Ewall . |
| 4,979,946 | 12/1990 | Gilman . |
| 4,983,173 | 1/1991 | Patience et al. . |
| 5,025,783 | 6/1991 | Lamb . |

FOREIGN PATENT DOCUMENTS

| | | |
|---|---|---|
| 48769/90 | 1/1990 | Australia . |
| 2367/80 | 11/1980 | Ireland . |
| 9003155 | 4/1990 | World Int. Prop. O. .......... 128/156 |

Primary Examiner—Randall L. Green
Assistant Examiner—Anthony P. Zuttarelli
Attorney, Agent, or Firm—Killworth, Gottman, Hagan & Schaeff

[57] ABSTRACT

A wound dressing for a deep wound is provided. The wound dressing comprises a hydrogel layer having an upper surface and a lower surface. The hydrogel layer is correspondingly sized to fill the cavity of the deep wound. The wound dressing further comprises a dressing removal layer disposed between the upper surface and the lower surface of the hydrogel layer. The dressing removal layer extends outwardly from the hydrogel layer so as to form a pull tab which facilitates removal of the hydrogel layer from the deep wound. A method of making a wound dressing for a deep wound is also provided.

14 Claims, 3 Drawing Sheets

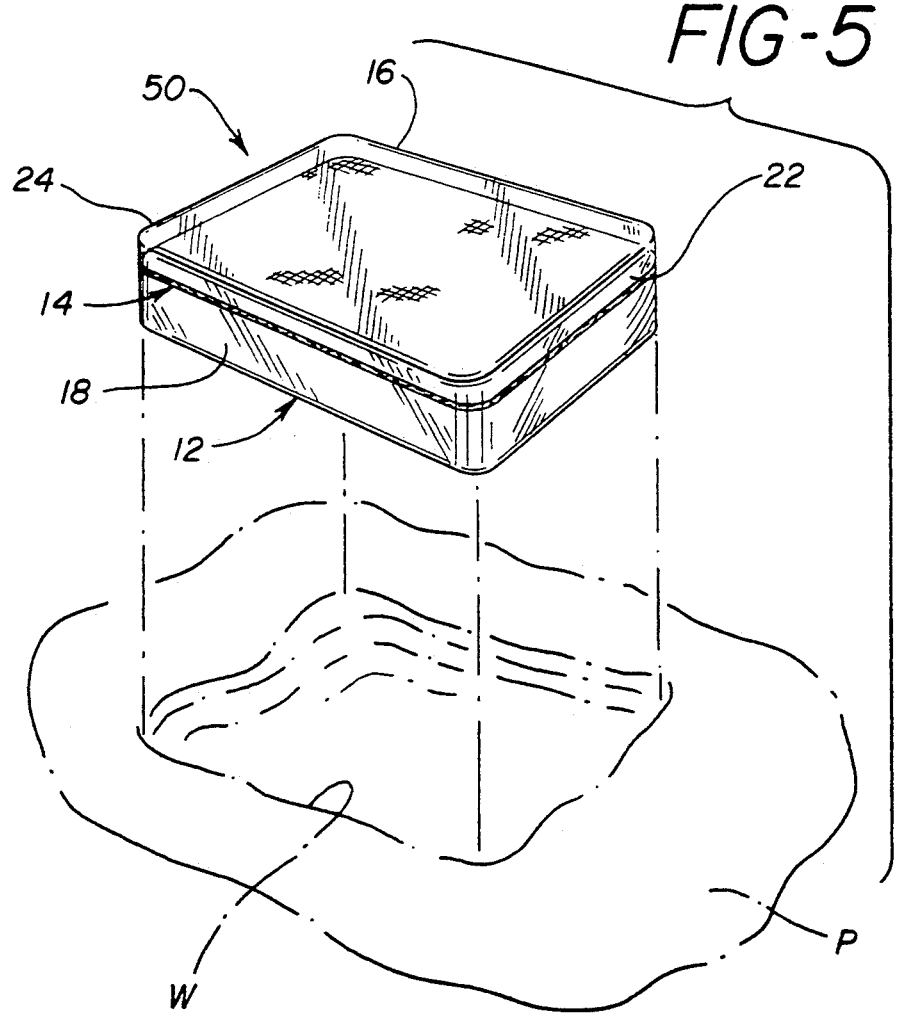
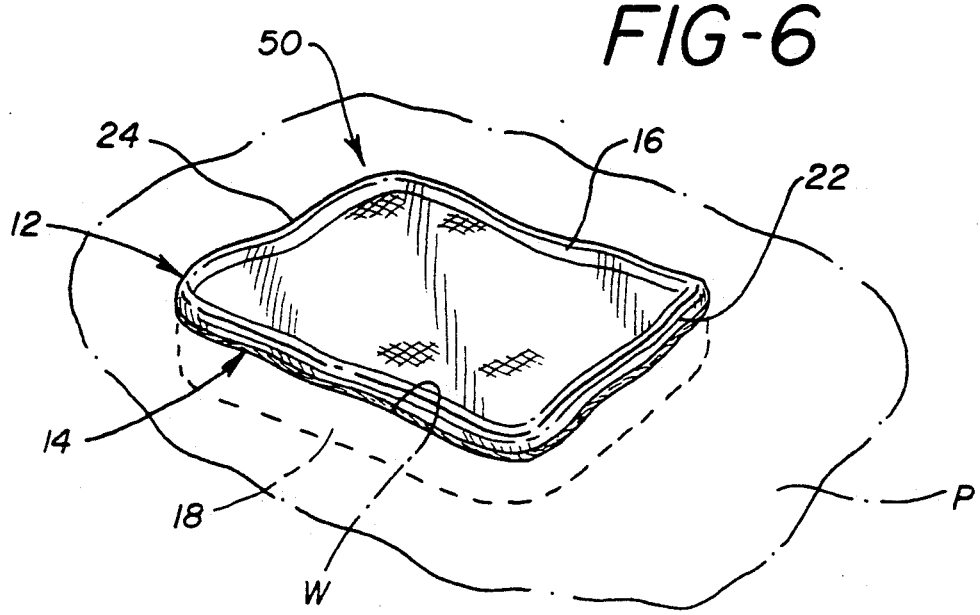

WOUND DRESSING FOR DEEP WOUNDS

BACKGROUND OF THE INVENTION

The present invention generally relates to wound dressings and, more particularly, to a wound dressing for deep wounds comprising a hydrogel layer and a dressing removal layer disposed therein.

Secreting skin wounds, such as decubitus ulcers and open surgical wounds, have long presented a medical challenge in keeping such wounds sterile and relatively dry. The accumulation of wound exudate, such as blood, pustulation, and other wound fluids, in wound crevices promotes growth of bacteria and crusted organisms which cause infection and delay the healing process. Such wound exudate may also cause maceration of tissue adjacent the wound and support infection thereof. However, since it is often desirable to allow a wound to heal in a slightly "moist" or occlusive state which is believed to accelerate healing, excess wound exudate must be removed. If excess wound exudate remains on a wound, a "blister" of exudate can form under the wound dressing which is not only unsightly, but also may cause the dressing to leak, thereby defeating the aim of sterility. However, existing methods of aspiration can lead to wound infection or can destroy sterility. Additionally, it is not desirable to remove all the exudate as that would result in a "dry" wound resulting in a slower healing process.

The art is replete with wound and/or surgical dressings for treating skin lesions, such as decubitus ulcers and open surgical wounds. For example, Mason, Jr. et al, U.S. Pat. No. 4,393,048, disclose a hydrogel wound treatment composition which dries to a powder after it is introduced into an open, draining wound to absorb wound exudate. However, dry hydrogel deteriorates as the wound fluids are absorbed resulting in lumping and uneven application. Additionally, such deteriorated lumps are difficult to remove from a wound site without damaging new cell tissue at the wound site. Furthermore, the progress of wound healing cannot be determined without removing, at least partially, the wound dressing from the wound site.

Aqueous moisture absorbing materials, such as a hydrogel material with a polyethylene glycol liquid curing agent as disclosed in Spence, U.S. Pat. No. 4,226,232, are easier to remove from the wound site, but cannot be sterilized by irradiation due to the formation of free radicals within the aqueous material. Another aqueous absorbing material used to absorb wound exudate is an hydrophilic polymer as disclosed in Rawlings et al, U.S. Pat. No. 4,657,006. Rawlings et al disclose a wound dressing which comprises a hydrophilic polymer having moisture and vapor permeability characteristics. However, a problem with the Rawlings et al wound dressing is that the wound exudate absorbed by the hydrophilic polymer hardens or solidifies the polymer, allowing pockets to develop between the polymer and the wound, thereby providing an excellent environment for bacteria proliferation.

Nor are existing wound dressings conducive for healing extremely deep wounds. It is not uncommon for certain deep wounds to extend down to the bones or tendons. These types of wounds are typically characterized as stage 3 or stage 4 wounds. The most severe wounds in terms of depth are characterized as stage 4 wounds. However, known wound dressings do not facilitate such deep wounds as exemplified by the wound dressings in Mason, Jr. et al, Spence, and Rawlings et al which are designed for treating surface wounds. Moreover, existing filler gel packs used to temporarily fill such deep wounds break apart in fragments upon removal from the wound. These filler gel packs are also difficult to wash out from the healing wound since there is a tendency for the filler material to adhere to the new cell tissue forming on the surface of the wound.

Accordingly, there is a need for a wound dressing especially conducive for deep wounds. There is also a need for a wound dressing for a deep wound which may be precut, sterilized, and readily available for application to a draining wound and which contains an exudate absorbing composition. Finally, there is a need for a wound dressing for a deep wound which may be removed neatly as a single piece without adhering to the new cell tissue of the wound.

SUMMARY OF THE INVENTION

The present invention meets the aforementioned needs by providing a wound dressing for a deep wound which may be characterized as a stage 3 or stage 4 wound which contains an exudate absorbing composition and which can be removed neatly without adhering to the new cell tissue in the wound.

In accordance with one aspect of the present invention, the wound dressing comprises a hydrogel layer having an upper surface and a lower surface which is correspondingly sized to fill the cavity created by the deep wound. The wound dressing further comprises a dressing removal layer disposed between the upper surface and the lower surface of the hydrogel layer. The dressing removal layer extends outwardly from the hydrogel layer so as to form a pull tab which facilitates removal of the hydrogel layer from the deep wound. In another aspect of the invention, a wound dressing product which includes the wound dressing in a tray correspondingly sized with the wound and a protective cover layer for sterility purposes is provided. The hydrogel layer comprises an aqueous mixture of polyhydric alcohol, isophoronediisocyanate terminated prepolymer, polyethylene oxide based diamine and sodium chloride. The dressing removal layer is made from a material selected from the group consisting of scrim, fabrics, fiber nettings and combinations thereof.

In accordance with yet another aspect of the present invention, a method of using the wound dressing is provided. The method of using comprises the step of providing a wound dressing for a deep wound including a hydrogel layer being correspondingly sized to fill the cavity of the deep wound, and a dressing removal layer disposed within the hydrogel layer. The dressing removal layer extends outwardly to form the pull tab which facilitates removal of the hydrogel layer from the deep wound. The method further comprises the steps of disposing the wound dressing in the deep wound, whereby the wound dressing product substantially fills the cavity of the deep wound, and removing the wound dressing product from the deep wound by pulling the pull tab of the dressing removal layer. Preferably, the wound dressing is removed as a single piece so as to minimize the destruction of the new cell tissue found in a healing deep wound.

In accordance with yet another aspect of the invention, a method of making the wound dressing is provided. The method of making comprises the steps of providing a tray for forming and storing the wound dressing, and pouring a first layer of a liquid hydrogel into the tray. The method further comprises the step of placing a dressing removal layer onto the first layer of liquid hydrogel such that the dressing removal layer extends outwardly from the first layer so as to form the pull tab. Next, the method includes the step of pouring a second layer of the liquid hydrogel onto the dressing removal layer so that the first layer and the second layer are correspondingly sized to fill the cavity of a deep wound. In an alternative method, the dressing removal layer may be disposed within the hydrogel layer by elevating it at the desired height within the tray. Thereafter, the liquid hydrogel may be poured into the tray through the dressing removal layer until the tray is filled to the desired level. The final step in either method involves allowing the liquid hydrogel to cure, thereby forming a solid wound dressing. The method may include the step of placing a protective cover layer over the tray in order to form a wound dressing product ready for commercial sales.

Accordingly, it is an object of the present invention to provide a wound dressing especially conducive for deep wounds; to provide a wound dressing for a deep wound which may be precut, sterilized, and be readily available for application to a draining deep wound; to provide a wound dressing which contains an exudate absorbing composition; and to provide a wound dressing for a deep wound which may be removed neatly as a single piece without adhering to the new cell tissue being formed in the deep wound. Other objects and advantages of the invention will be apparent from the following detailed description, the accompanying drawings and the appended claims.

BRIEF DESCRIPTION OF THE DRAWINGS

FIG. 5 is an exploded perspective view of another embodiment 50 of the wound dressing 10 in accordance with the invention; and FIG. 6 is a perspective view of the wound dressing 50 disposed in the wound W.

DETAILED DESCRIPTION OF THE PREFERRED EMBODIMENT

Figure 1:
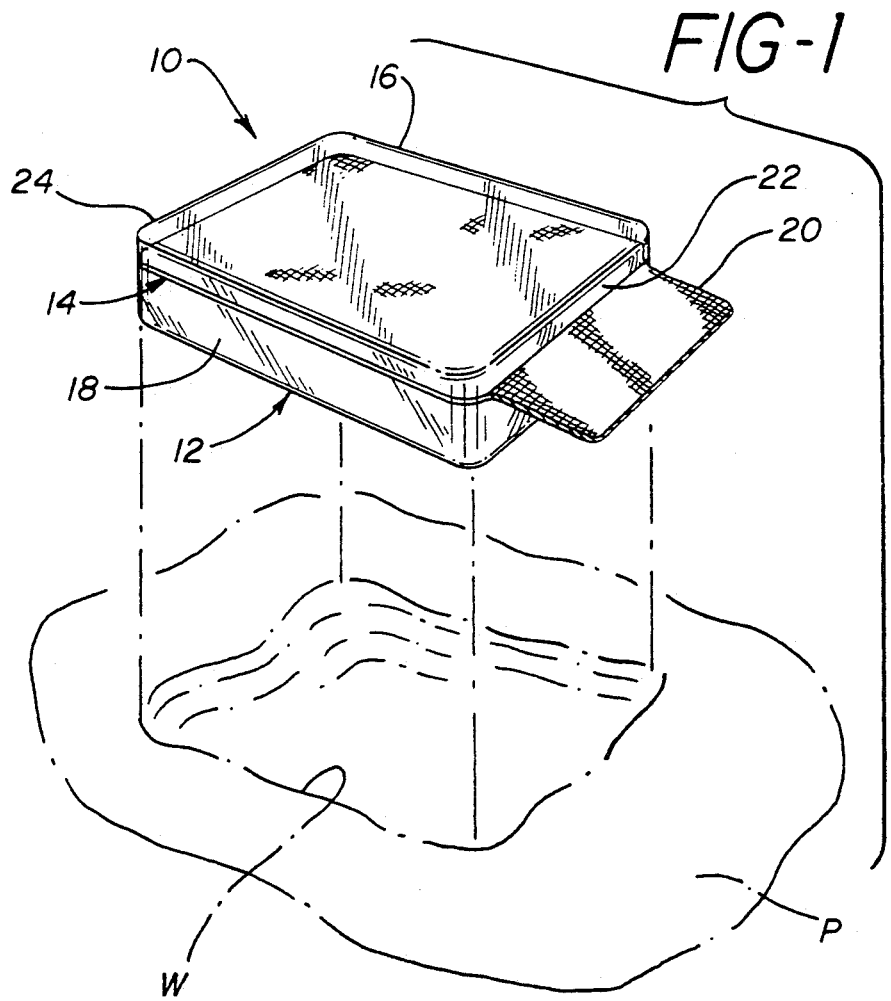
FIG. 1 is an exploded perspective view of the wound dressing 10 for the wound W of the patient P.

The present invention relates to a wound dressing 10 for application to a deep wound W on a patient P. A perspective view of the wound dressing 10 is illustrated in FIG. 1. The wound dressing 10 generally comprises a hydrogel layer 12 and a dressing removal layer 14. The hydrogel layer 12 has an upper surface 16 and a lower surface 18 which define the thickness of the hydrogel layer 12. The thickness of the hydrogel layer 12 is sufficient enough to fill the cavity created by the wound W. The wound W is relatively deep and may be characterized as a stage 3 or stage 4 wound. A deep wound characterized as a stage 3 or stage 4 wound is an extremely deep wound extending well below the surface of the skin. For example, a stage 4 wound extends down to the bones and tendons and may have a depth ranging from 16 cm to 18 cm. The present invention provides the wound dressing 10 which is especially conducive for such deep wounds.

The dressing removal layer 14 includes a pull tab 20 to facilitate removal of the wound dressing 10 from the wound W. The tab 20 extends outwardly from the hydrogel layer 12 so as to provide a means for pulling the wound product 10 out from the wound W. It should be understood that the dressing removal layer 14 may be positioned at any depth within the hydrogel layer 12. Preferably, the dressing removal layer 14 is at a depth such that the entire wound dressing 10 can be removed from the wound W as a single piece by pulling the tab 20. Additionally, the actual size of the dressing removal layer 14, as disposed within the hydrogel layer 12, is sufficient to facilitate removal of the hydrogel layer 12 from the wound W. Preferably, the wound dressing 10 is removed as a single piece rather than in fragmental pieces. Removal of the wound dressing 10 as a single piece is more conducive for the healing process since destruction of the new cell tissue forming in the wound W is minimized as the wound dressing 10 is removed.

The removal of the wound dressing 10 from a wound W characterized as a stage 4 wound is facilitated further by the preferred hydrogel composition used to form the hydrogel layer 12. In that regard, the preferred hydrogel layer 12 comprises an aqueous mixture of polyhydric alcohol, isophoronediisocyanate terminated prepolymer, polyethylene oxide based diamine and sodium chloride. Preferably, the polyhydric alcohol is selected from the group consisting of polypropylene glycol, polyethylene glycol and glycerine. By forming the hydrogel layer 12 from the aforementioned aqueous mixture, the wound dressing 10 remains intact as it absorbs wound exudate from the wound W. Furthermore, the hydrogel layer 12 does not adhere or stick to the wound W which allows for easy removal of the wound dressing 10. Additionally, the biocompatibility of the hydrogel layer 12 within the wound W is extremely favorable. Such characteristics are especially important for deep wounds characterized as stage 3 and stage 4 wounds.

A more preferred hydrogel composition for the hydrogel layer 12 comprises an aqueous mixture including from about 0% to about 90% by weight polyhydric alcohol; from about 6% to about 60% by weight isophoronediisocyanate terminated prepolymer; from about 4% to about 40% by weight polyethylene oxide based diamine; up to about 2% by weight sodium chloride; and the balance water. A most preferred hydrogel composition for forming the hydrogel layer 12 comprises an aqueous mixture having from about 15% to about 30% by weight polypropylene glycol; from about 8% to about 14% by weight isophoronediisocyanate terminated prepolymer; from about 5% to about 10% by weight polyethylene oxide based diamine; and up to about 1% by weight sodium chloride; and the balance water. Most preferably, the polyurethane hydrogel material comprises: (a) from about 16% to 17% by weight polypropylene glycol; (b) from about 10% to 12% by weight isophoronediisocyanate terminated prepolymer; (c) from about 7% to 9% by weight polyethylene oxide based diamine; (d) about 0.5% to 1% by weight sodium chloride; and (e) the balance water.

The isophoronediisocyanate terminated polymer is preferably based on polyols containing more than about 40% polyethylene oxide and having an isocyanate content of about 3% by weight. The molecular weight is preferably in a range from 1500-8000 and most preferably, from about 4000 to 5000. The molecular weight of the polyethylene oxide based diamine is preferably in a range from about 200 to 6000 and most preferably, about 2000. Those skilled in the art will appreciate that all of the constituents with the preferred hydrogel material may be readily synthesized or purchased commercially. The aforementioned preferred hydrogel compositions provide a wound dressing 10 having the desired properties of excellent biocompatibility and absorption of exudate properties without adhering to the wound W. However, other materials having such characteristics, including but not limited to the aforementioned hydrogel compositions, may be used to form the hydrogel layer 12 in accordance with the present invention.

The dressing removal layer 14 is preferably made from a material selected from the group consisting of scrim, fabrics, fiber nettings and combinations thereof. However, the material used to form the dressing removal layer 14 may include any material which can be characterized as flexible, non-toxic to the human body, and capable of adhering to the hydrogel layer 12, even after a substantial amount of wound exudate has been absorbed into the wound dressing 10. The material must be flexible so as to allow the tab 20 to be pulled away from the surface of the skin. It is preferable to use a non-toxic material to eliminate or minimize the likelihood of toxic poisoning through the skin or directly in the wound W. Additionally, the material must have the ability to adhere to the hydrogel layer 12 even when exposed to a substantial amount of wound exudate in order to permit the removal of the wound dressing 10 Therefore, any material in addition to the aforementioned materials may be used in accordance with the invention. Most preferably, the dressing removal layer is made from a fabric such as textured polyester or a scrim material, both of which are commercially available.

The wound dressing 10 includes the hydrogel layer 12 having the dressing removal layer 14 disposed therein between the upper surface 16 and the lower surface 18 of the wound dressing 10. As can be seen in FIG. 1, the dressing removal layer 14 extends outwardly from a first side 22 of the hydrogel layer 12 to form the tab 20. It should be understood that it is possible to have a second tab (not shown) extending from a second side 24 of the hydrogel layer 12 to provide an additional means for removing the wound dressing 10 from the wound W.

Figure 2:
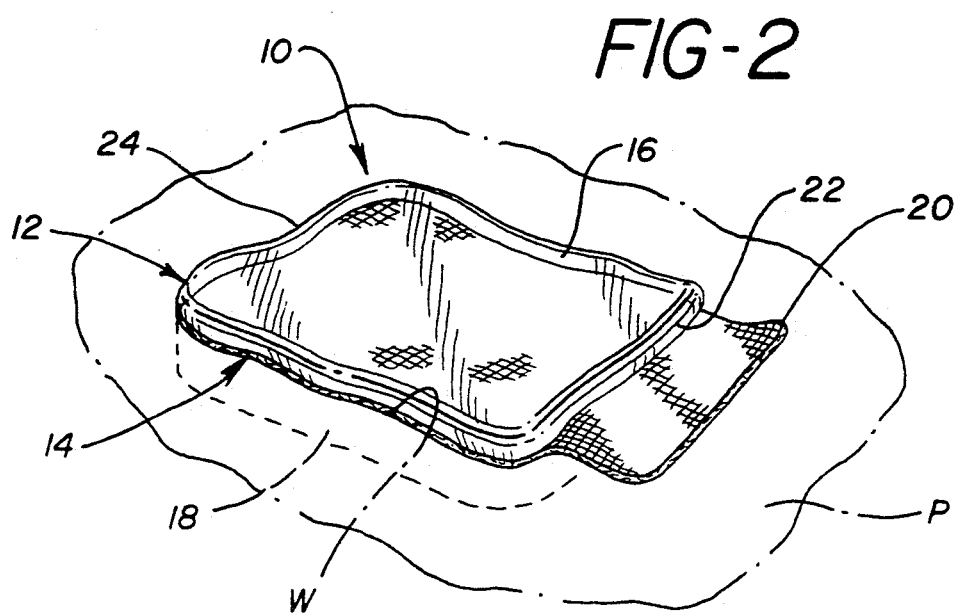
FIG. 2 is a perspective view of the wound dressing 10 disposed in the wound W.

The present invention also relates to a method of using the wound dressing 10 as illustrated in FIGS. 1-2. The first step of the method of using the wound dressing 10 is illustrated in FIG. 1. The first step provides the wound dressing 10 which is adapted for the wound W such that the hydrogel layer 12 is correspondingly sized to fill the cavity thereof. Additionally, the dressing removal layer 14 includes the tab 20 to facilitate removal from the wound W. As best seen in FIG. 2, the wound dressing 10 is disposed into the wound W of the patient P, whereby the wound dressing 10 substantially fills the cavity created by the wound W. After the healing process has progressed sufficiently, the wound dressing 10 is removed from the wound W by pulling the tab 20. Preferably, the wound dressing 10 is removed neatly as a single piece, thereby minimizing the destruction of the healing wound. The exact time at which the wound dressing 10 is removed from the patient P is determined by the attending medical personnel. It should be appreciated, however, that the healing process of the wound W is accelerated by the use of the wound dressing 10.

Figure 3A:
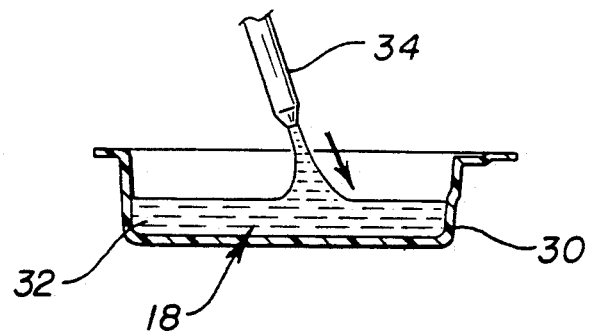
FIGS. 3A-3C are schematic views of the wound dressing 10 as it is prepared in accordance with the invention.
Figure 3B:
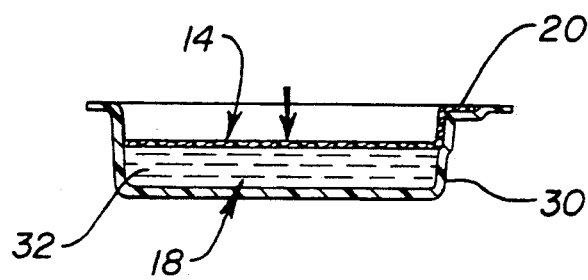
Figure 3C:
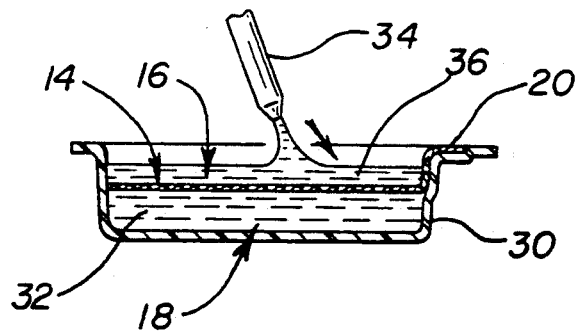
Figure 4:
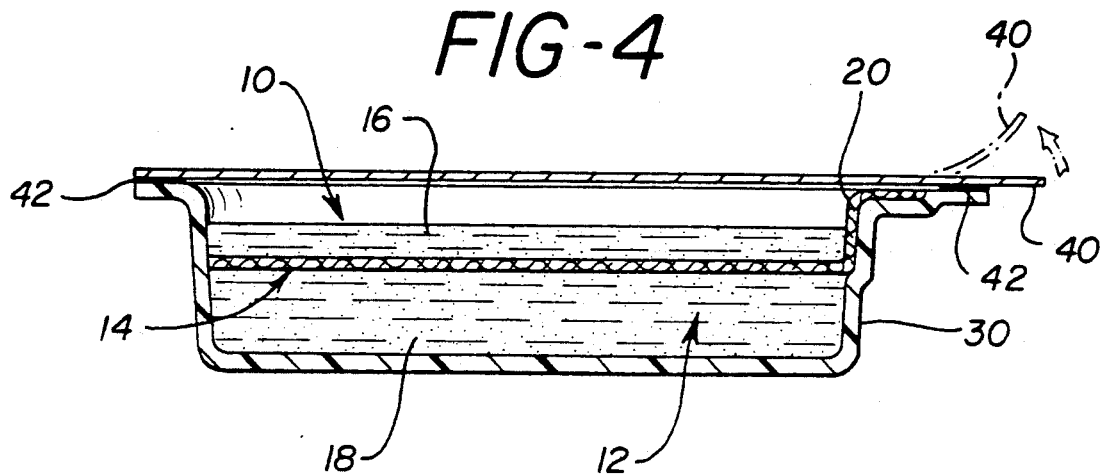
FIG. 4 is a schematic view of the wound dressing product 50 containing the wound dressing 10 in accordance with the invention.

The present invention also relates to a method of making the wound dressing 10 and a wound dressing product 50 as illustrated in FIG. 4. FIGS. 3A-3C illustrate a sequential method of making the wound dressing 10 in accordance with the invention. The first step of the method is illustrated in FIG. 3A wherein a tray 30 is provided for forming and storing the wound dressing 10. A first layer 32 of the preferred hydrogel composition in the liquid phase is poured into the tray 30 from a nozzle 34 or a functionally similar apparatus. The tray 30 will have a size large enough to fill the cavity of most wounds found on the patient P. Alternatively, the tray 30 may have a series of sizes corresponding to a variety of wound dimensions. It should be understood that the wound dressing 10 may be cut or skived to the size of the particular wound W found on the patient P. Further, the tray 30 may be formed from any compatible material. Preferably, the material is selected from the group consisting of polystyrene, silicon-coated polystyrene and polyethylene.

As shown in FIG. 3B, the dressing removal layer 14 is placed on the first layer 32 such that the dressing removal layer 14 extends from the first layer 32 to form the pull tab 20. As discussed above, it should be understood that the size and location of the dressing removal layer 14 may vary in accordance with the invention. The liquid hydrogel in the first layer 14 permeates through the interstices of the dressing removal layer 14, thereby adhering the dressing removal layer 14 securely to the first layer 32. A second layer 36 of the preferred hydrogel composition in the liquid phase is poured from the nozzle 34 onto the dressing removal layer 14 as illustrated in FIG. 3C. The liquid hydrogel from the second layer 36 permeates through any remaining interstices down into the first layer 32 such that the second layer 36 adheres to the dressing removal layer 14. In an alternative method, the dressing removal layer 14 may be elevated within the tray 30 and thereafter, the liquid hydrogel is poured into the tray 30 through the interstices of the dressing removal layer 14 until the tray 30 is filled. In both of the aforementioned methods, the preferred hydrogel composition is then allowed to cure. More specifically, the cure time for the preferred hydrogel composition is in a range from approximately 6 minutes to approximately 8 minutes. However, it should be understood that the exact cure time will depend upon the particular hydrogel constituents used and their relative compositions.

FIG. 4 illustrates the wound dressing product 50 which includes the wound dressing 10 in accordance with the invention. After the first layer 32 and the second layer 36 have solidified, a protective cover layer 40 is placed over the tray 30. Preferably, the protective cover layer 40 is made from a material selected from the group consisting of synthetic polymers, foils and polymer-foil laminates. Those skilled in the art will appreciate that the protective cover layer 40 may be formed from other materials without departing from the scope of the invention. The protective cover layer 40 is adhered to the tray with an adhesive 42 applied around at least a portion of the periphery of the tray 30. The adhesive 42 may be formed from any adhesive materials capable of adhering the protective cover layer 40 to the tray 30 yet permit the easy removal of the protective cover layer 40 as shown in FIG. 4. Many adhesives of this character are commercially available.

The particular size of the wound dressing product 50 may vary significantly in view of the multitude of possible wound sizes which may be found on the patient P. However, as discussed above, the aggregate thickness of the wound dressing 10, as contained in the wound dressing product 50, is sufficient to fill the cavity of a stage 3 or stage 4 wound. Accordingly, the wound dressing 10 preferably has a thickness in range from approximately 1 cm to 18 cm. The length and width of the wound dressing 10 will correspond to the size of the wound W. If the dimensions of the wound dressing 10 are not exact after removal from the tray 30, the wound dressing 10 may be cut or skived so as to be correspondingly sized with the wound W on the patient P.

Referring now to FIG. 5, yet another embodiment 50 of a wound dressing in accordance with the invention is illustrated. The wound dressing 50 is substantially identical in all respects to the wound dressing 10, except that the wound dressing 50 does not include the pull tab 20. Rather, the wound dressing 50 is removed from the wound W by any means which will separate the wound dressing 50 from the wound W without causing substantial damage to the healing wound. For example, medical personnel may use a pair of tweezers or similar device to carefully remove the wound dressing 50 from the wound W. It should be understood that the wound dressing 50 may be made in accordance with any of the methods described above with respect to the wound dressing 10. Those skilled in the art will appreciate that the dressing removal layer 14 provides support for the hydrogel layer 12 and may be positioned at any depth within the wound dressing 50.

FIG. 6 illustrates the wound dressing 50 while disposed in the wound W of the patient P. As seen in FIG. 6, it is preferable for at least a portion of the hydrogel layer 12 to extend slightly above the surface of the skin of the patient P so as to facilitate removal of the wound dressing 50 from the wound W. The wound dressing 50 is especially easy to size to the shape of the wound W since it does not include the pull tab 20. For example, the wound dressing 50 may be packaged in the form of a sheet or similar configuration and then, cut or skived to the shape of the wound W found on the patient P. Of course, a wide variety of other forms of packaging of the wound dressing 50 may be contemplated by those skilled in the art without departing from the scope of the invention. It should be understood that all of the aforedescribed materials used in the wound dressing 10 are employed in the wound dressing 50, as well.

Having thus described the invention in detail by way of reference to the preferred embodiments, it will be apparent that other modifications and variations are possible without departing from the scope of the appended claims. For example, the dressing removal layer 14 may have a different size and may be positioned elsewhere within the wound dressing product 10 as compared to the dressing removal layer 14 shown in FIGS. 1-4.

What is claimed is:

1. A wound dressing for a deep open surgical wound comprising:

a hydrogel layer having an upper surface and a lower surface, said hydrogel layer having a thickness in a range from about 1 cm to about 18 cm such that said lower surface of said hydrogel layer can extend into said deep open surgical wound such that said hydrogel layer a self-adheres to said deep open surgical wound; and a dressing removal layer disposed between said upper surface and said lower surface of said hydrogel layer, said dressing removal layer extending outwardly from said hydrogel layer so as to form a pull tab which facilitates removal of said hydrogel layers from said deep open surgical wound.

2. A wound dressing as claimed in claim 1 wherein said dressing removal layer is made from a material selected from the group consisting of fabrics, fiber nettings, scrim and combinations thereof.

3. A wound dressing as claimed in claim 1 wherein said dressing removal layer is made from a textured polyester.

4. A wound dressing for a deep open surgical wound comprising:

a hydrogel layer having an upper surface and a lower surface, said hydrogel layer having a thickness in a range from about 1 cm to about 18 cm such that said lower surface of said hydrogel layer can extend into said deep open surgical wound such that said hydrogel layer self-adheres to said deep open surgical wound; and a dressing removal layer disposed between said upper surface and said lower surface of said hydrogel layer such that said hydrogel layer can be removed from said deep open surgical wound as substantially a single piece.

5. A wound dressing as claimed in claim 4 wherein said dressing removal layer is made from a material selected from the group consisting of fabrics, fiber nettings, scrim and combinations thereof.

6. A wound dressing product for a deep open surgical wound comprising:

(a) a tray for forming and storing said wound dressing;
    (b) a hydrogel layer having an upper surface and a lower surface disposed in said tray, said hydrogel layer having a thickness in a range from about 1 cm to about 18 cm such that said lower surface of said hydrogel layer can extend into said deep open surgical wound such that said hydrogel layer is self-adhered to said deep open surgical wound;
    (c) a dressing removal layer disposed between said upper surface and said lower surface of said hydrogel layer, said dressing removal layer extending outwardly from said hydrogel layer so as to form a pull tab which facilitates removal of said hydrogel layer from said deep open surgical wound; and
    (d) a protective cover layer over said tray for preventing contaminants from contacting said hydrogel layer.

7. A wound dressing product as claimed in claim 6 wherein said hydrogel layer is an aqueous mixture comprising:

(a) from about 0% to about 90% by weight polyhydric alcohol;
    (b) from about 6% to about 60% by weight isophoronediisocyanate terminated prepolymer;
    (c) from about 4% to about 40% by weight polyethylene oxide based diamine;
    (d) up to about 2% by weight sodium chloride; and
    (e) the balance water.

8. A wound dressing product as claimed in claim 6 wherein said dressing removal layer is made from a material selected from the group consisting of fabrics, fiber nettings, scrim and combinations thereof.

9. A wound dressing for a deep open surgical wound comprising:
 a hydrogel layer having an upper surface and a lower surface such that said hydrogel layer self-adheres to said deep open surgical wound, said hydrogel layer being formed from an aqueous mixture comprising
 (a) from about 0% to about 90% by weight polyhydric alcohol;
 (b) from about 6% to about 60% by weight isophoronediisocyanate terminated prepolymer;
 (c) from about 4% to about 40% by weight polyethylene oxide based diamine;
 (d) up to about 2% by weight sodium chloride; and
 (e) the balance water; and
 a dressing removal layer disposed between said upper surface and said lower surface of said hydrogel layer, said dressing removal layer extending outwardly from said hydrogel layer so as to form a pull tab which facilitates removal of said hydrogel layer from said deep open surgical wound.

10. A wound dressing as claimed in claim 9 wherein said polyhydric alcohol is selected from the group consisting of polypropylene glycol, polyethylene glycol and glycerine.

11. A wound dressing for a deep open surgical wound comprising:
 a hydrogel layer having an upper surface and a lower surface such that said hydrogel layer self-adheres to said deep open surgical wound, said hydrogel layer being formed from an aqueous mixture comprising
 (a) from about 0% to about 90% by weight polyhydric alcohol;
 (b) from about 6% to about 60% by weight isophoronediisocyanate terminated prepolymer;
 (c) from about 4% to about 40% by weight polyethylene oxide based diamine;
 (d) up to about 2% by weight sodium chloride; and
 (e) the balance water; and
 a dressing removal layer disposed between said upper surface and said lower surface of said hydrogel layer.

12. A wound dressing as claimed in claim 11 wherein said polyhydric alcohol is selected from the group consisting of polypropylene glycol, polyethylene glycol and glycerine.

13. A wound dressing for a deep open surgical wound comprising:
 a hydrogel layer having an upper surface and a lower surface such that said hydrogel layer self-adheres to said deep open surgical wound, said hydrogel layer being formed from an aqueous mixture comprising
 (a) from about 15% to about 30% by weight polyhydric alcohol;
 (b) from about 8% to about 14% by weight isophoronediisocyanate terminated prepolymer;
 (c) from about 5% to about 10% by weight polyethylene oxide based diamine;
 (d) up to about 1% by weight sodium chloride; and
 (e) the balance water; and
 a dressing removal layer disposed between said upper surface and said lower surface of said hydrogel layer, said dressing removal layer extending outwardly from said hydrogel layer so as to form a pull tab which facilitates removal of said hydrogel layer from said deep open surgical wound.

14. A wound dressing for a deep open surgical wound comprising:
 a hydrogel layer having an upper surface and a lower surface such that said hydrogel layer self-adheres to said deep open surgical wound, said hydrogel layer being formed from an aqueous mixture comprising
 (a) from about 15% to about 30% by weight polyhydric alcohol;
 (b) from about 8% to about 14% by weight isophoronediisocyanate terminated prepolymer;
 (c) from about 5% to about 10% by weight polyethylene oxide based diamine;
 (d) up to about 1% by weight sodium chloride; and
 (e) the balance water; and
 a dressing removal layer disposed between said upper surface and said lower surface of said hydrogel layer.

* * * * *

UNITED STATES PATENT AND TRADEMARK OFFICE
CERTIFICATE OF CORRECTION

PATENT NO. : 5,154,706
DATED : October 13, 1992
INVENTOR(S) : James V. Cartmell et al It is certified that error appears in the above-identified patent and that said Letters Patent is hereby corrected as shown below:

Col. 8, line 1,     "layer a self-adheres" should read
                    --layer self-adheres--.

Col. 8, line 8,     "layers from said" should read
                    --layer from said--.

Signed and Sealed this

Second Day of November, 1993

Attest:

BRUCE LEHMAN

*Attesting Officer*     Commissioner of Patents and Trademarks